(12) United States Patent
Sauter-Starace et al.

(10) Patent No.: US 10,863,643 B2
(45) Date of Patent: Dec. 8, 2020

(54) IMPLANTABLE MEDICAL DEVICE HAVING AN IMPROVED ARCHITECTURE

(71) Applicant: Commissariat A L'Energie Atomique et aux Energies Alternatives, Paris (FR)

(72) Inventors: Fabien Sauter-Starace, Grenoble (FR); Alice Siegel, Grenoble (FR)

(73) Assignee: Commissariat A L'Energie Atomique et aux Energies Alternatives, Paris (FR)

( * ) Notice: Subject to any disclaimer, the term of this patent is extended or adjusted under 35 U.S.C. 154(b) by 0 days.

(21) Appl. No.: 16/703,989

(22) Filed: Dec. 5, 2019

(65) Prior Publication Data

US 2020/0187375 A1    Jun. 11, 2020

(30) Foreign Application Priority Data

Dec. 7, 2018 (FR) .................................. 18 72524

(51) Int. Cl.
*A61N 1/375* (2006.01)
*H05K 5/06* (2006.01)
(Continued)

(52) U.S. Cl.
CPC ........... *H05K 5/069* (2013.01); *A61N 1/3758* (2013.01); *H05K 7/1427* (2013.01); *H05K 7/2039* (2013.01); *H05K 7/20454* (2013.01)

(58) Field of Classification Search
CPC .. A61N 1/3758; G06F 1/1656; H05K 5/0056; H05K 5/069; H05K 7/1427; H05K 7/2039; H05K 7/20454; H05K 2201/2045
See application file for complete search history.

(56) References Cited

U.S. PATENT DOCUMENTS

| 5,768,104 A | * | 6/1998 | Salmonson | ........ H05K 7/20454 |
|---|---|---|---|---|
| | | | | 257/714 |
| 2001/0033476 A1 | * | 10/2001 | Dibene, II | .............. G06F 1/189 |
| | | | | 361/702 |

(Continued)

FOREIGN PATENT DOCUMENTS

| CN | 106512213 A | 3/2017 |
|---|---|---|
| FR | 2 898 462 A1 | 9/2007 |
| WO | WO 2006/081361 A2 | 8/2006 |

OTHER PUBLICATIONS

French Preliminary Search Report dated Nov. 4, 2019 in French Application 18 72524 filed on Dec. 7, 2018 (with English Translation of Categories of Cited Documents & Written Opinion), 9 pages.

*Primary Examiner* — Jacob R Crum
(74) *Attorney, Agent, or Firm* — Oblon, McClelland, Maier & Neustadt, L.L.P.

(57) ABSTRACT

An implantable medical device including a hermetic housing, at least one electronic board housed in the housing, a module for heat dissipation and shock absorption, housed in the housing and arranged between the electronic board and an internal wall of the housing, the module having a first layer of thermal paste placed in the internal space of the housing and deposited on the electronic board, a second, metal layer of high thermal conductivity deposited on the first layer, a third layer of thermal paste deposited on the second layer and positioned so as to come into contact with the internal wall of the housing, the third layer having a structure with a plurality of cavities distributed over the entire area of contact of the third layer with the internal wall of the housing.

10 Claims, 5 Drawing Sheets

(51) Int. Cl.
  *H05K 7/14*    (2006.01)
  *H05K 7/20*    (2006.01)

(56) References Cited

U.S. PATENT DOCUMENTS

| | | | |
|---|---|---|---|
| 2009/0034769 A1 | 2/2009 | Darley et al. | |
| 2014/0078679 A1* | 3/2014 | Tsunoda | H05K 7/20445 |
| | | | 361/720 |
| 2014/0328024 A1* | 11/2014 | Mataya | H05K 7/20454 |
| | | | 361/720 |
| 2015/0069621 A1* | 3/2015 | Weatherspoon | |
| | | | H01L 23/49805 |
| | | | 257/774 |
| 2017/0127543 A1* | 5/2017 | Day | H01M 2/30 |
| 2017/0281936 A1* | 10/2017 | Aghassian | A61N 1/375 |
| 2018/0277970 A1* | 9/2018 | Shah | A61N 1/3752 |
| 2019/0364696 A1* | 11/2019 | Mujcinovic | H05K 5/0039 |

* cited by examiner

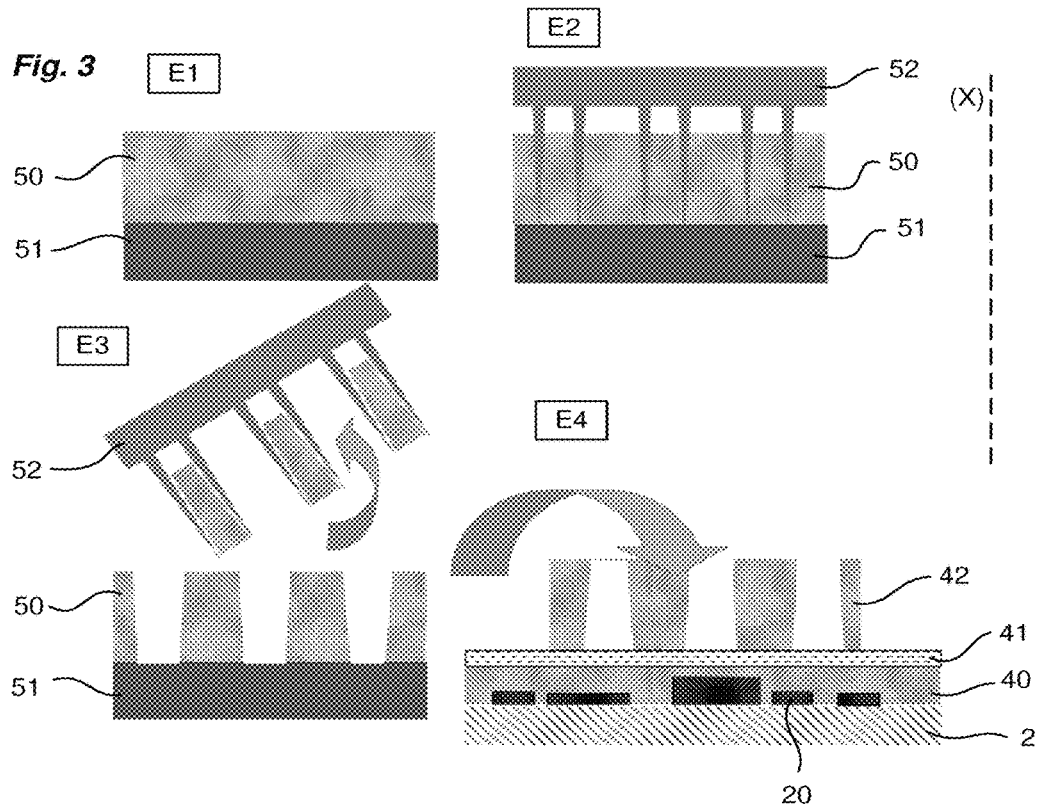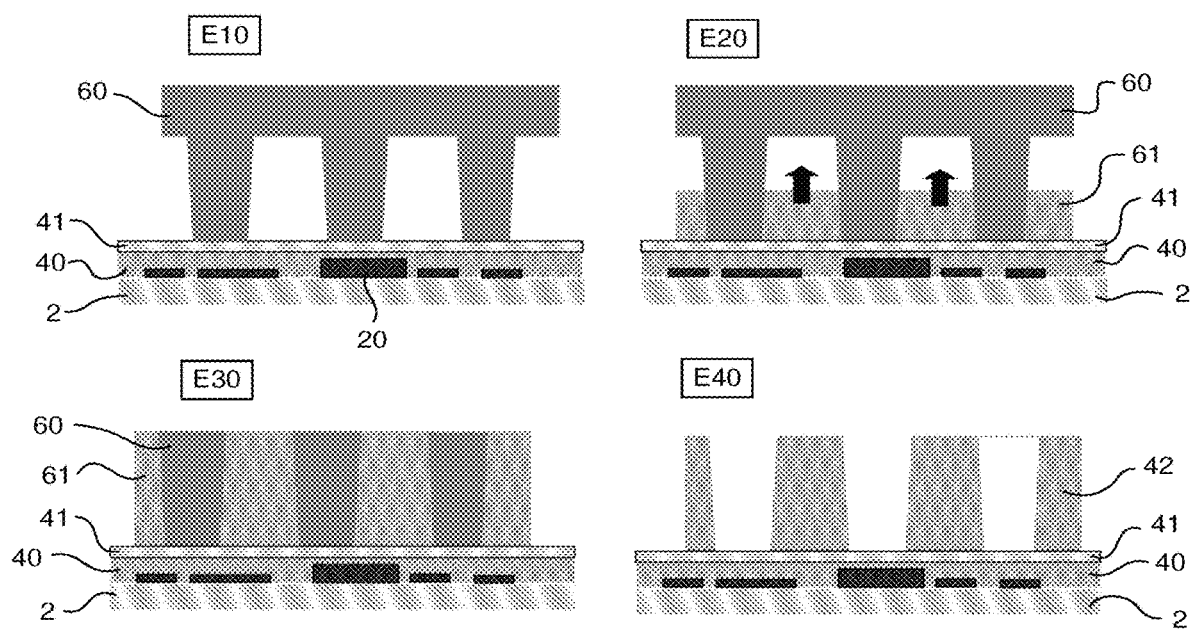

IMPLANTABLE MEDICAL DEVICE HAVING AN IMPROVED ARCHITECTURE

TECHNICAL FIELD OF THE INVENTION

The present invention relates to an implantable medical device. The implantable medical device of the invention has the particular feature of being very shock-resistant.

PRIOR ART

In the field of active implantable medical devices (known as AIMDs), in particular intracranial implants such as brain-machine interfaces, cochlear implants and neurostimulators, it is necessary to satisfy certain constraints:
- the housing of the device has to be hermetic so as to protect the patient from possible biological risks unintentionally caused by the AIMD and to avoid damaging the internal electronics;
- the device also has to be capable of dissipating the heat generated by the operation of the internal electronics;
- the device has to be capable of withstanding shocks. In the event of shocks, these devices have to maintain their integrity to the greatest possible extent and must not injure the brain or the skull.

The patent application WO2006/081361A2 relates to cochlear implants. It describes a device that has a hermetic container in which the electronics of the device are placed, a cover being affixed to the hermetic container and defining a non-hermetic internal space with said container. The patent application specifies that a material including silicone can be injected into this internal space in order notably to reinforce the shock resistance of the device.

However, the architecture proposed in that document is not satisfactory since it is unable to satisfy all of the constraints set out above. Specifically, it does not allow good heat dissipation since the electronics are isolated in the hermetic container, no solution being provided for dissipating the heat generated during operation. Moreover, it is unable to respond to the different types of shock that may arise and that may cause elastic deformations or plastic deformations of the device.

Therefore, the aim of the invention is to propose an implantable medical device that is capable of remedying the drawbacks of the prior art and can satisfy the various operating constraints listed above.

SUMMARY OF THE INVENTION

This aim is achieved by an implantable medical device comprising:
- a hermetic housing defining an internal space,
- at least one electronic board housed in said internal space of the housing, said board supporting electronic components,
- a module for heat dissipation and shock absorption, housed in the internal space of the housing and arranged between said electronic board and an internal wall of the housing, said module for heat dissipation and shock absorption having:
- a first layer of thermal paste placed in the internal space of the housing and deposited on said electronic board,
- a second, metal layer of high thermal conductivity deposited on said first layer,
- a third layer of thermal paste deposited on said second layer and positioned so as to come into contact with said internal wall of the housing, said third layer having a structure with a plurality of cavities distributed over the entire area of contact of the third layer with the internal wall of the housing.

According to one particular embodiment, the structure of the third layer is realized in the form of a plurality of concentric cavities.

According to another particular embodiment, the structure of the third layer has a plurality of parallel rectilinear cavities that form trenches and a comb structure having a plurality of teeth of given height and width.

According to another particular embodiment, the structure of the third layer has a spiral.

According to one particular feature of the device, each cavity of the structure is a through-cavity.

According to another particular feature, the second layer is formed of a metal of high thermal conductivity such as copper, gold or aluminium.

According to another particular feature, the thermal paste of the first layer and of the third layer has a thermal conductivity of between 1 and 12 W/m/K.

According to another particular feature, the first layer and the third layer include filled silicone.

According to another particular feature, the module for heat dissipation and shock absorption includes one or more additional layers made of pyrolytic graphite that are deposited under the second layer and between the third layer and the internal wall of the housing.

The invention also relates to a method for manufacturing an implantable medical device as defined above, wherein the structure of the third layer is produced by applying punches to a layer of thermal paste deposited on a substrate, by compression moulding or by injection moulding in a chemically soluble or thermally liquefiable mould.

BRIEF DESCRIPTION OF THE FIGURES

Further features and advantages will become apparent from the following detailed description given with reference to the appended drawings, in which:

FIGS. 3 to 5 respectively show three methods for producing the structured third layer employed in the device of the invention.

DETAILED DESCRIPTION OF AT LEAST ONE EMBODIMENT

Figure 1A:
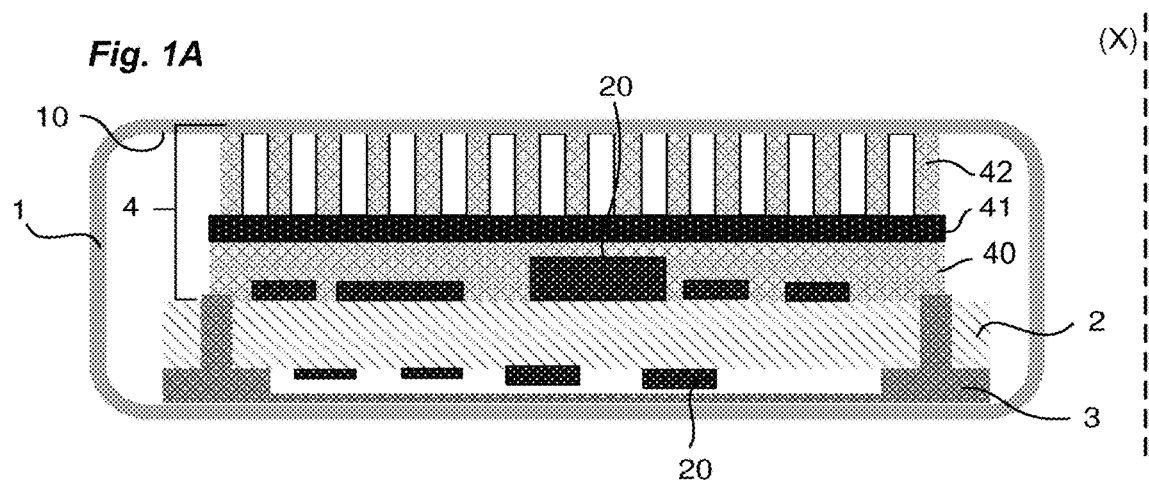
FIG. 1A shows, schematically in cross section, the architecture of the implantable medical device according to the invention.

In the rest of the description and in the drawings, the terms "top", "bottom", "upper", "lower", "above", "below" or equivalent terms should be understood considering a main axis (X) drawn vertically.

The solution of the invention applies mainly to active implantable medical devices (AIMDs), in particular those of high energy consumption. Implantable stimulators of the "pacemaker" type have been the subject of numerous improvements and consume very little electrical energy (a few μW) and therefore dissipate very little heat. By contrast, recording systems of the BCI ("Brain Computer Interface") type consume up to 350 mW (see the publication "Mestais, C. S., Charvet, G., Sauter-Starace, F., Foerster, M., Ratel, D., & Benabid, A. L. (2015), *WIMAGINE: wireless 64-channel ECoG recording implant for long term clinical applications. IEEE transactions on neural systems and rehabilitation engineering, 23*(1), 10-21"). For these devices, the problem of efficient and uniform extraction of energy therefore becomes critical.

With reference to FIG. 1A, an implantable medical device according to the invention has a housing 1 that can be made in two parts that are joined together, a first part, known as the lower part, forming a container, and a second part, known as the upper part, forming a cover that is positioned on the container. When the two parts are joined together, the housing 1 is closed hermetically and defines an internal space isolated from the outside. The hermeticity between the two parts can be realized by any known means.

For operation, the device has an electronic board 2. The electronic board 2 has two faces, each of its faces being able to support one or more electronic components 20.

The device may have a frame 3 housed in the bottom of one of the two parts of the housing 1, to which the electronic board 2 is fastened. In FIG. 1A, the frame 3 is positioned in the bottom of the container. The board 2 is mounted with its lower face on the frame and can be fastened to the frame 3 by any appropriate means. The frame 3 can be an independent piece fastened in the bottom of the container of the housing, for example via screws, or moulded directly with the container of the housing so as to have support members for the electronic board 2.

In the internal space of the housing, the implantable medical device also has a module 4 for heat dissipation and shock absorption.

This module 4 has an assembly of a plurality of superposed layers 40, 41, 42. The assembly of superposed layers has a lower face deposited on the upper face of the electronic board 2, on the opposite side of the latter from its lower face for fastening to the frame 3, and an upper face against which the internal wall 10 of the upper part of the housing 1 comes into contact, making it possible to wedge the device for heat dissipation and shock absorption in the housing and to serve as a shock absorber when the housing is subjected to shocks on its upper face.

The module for heat dissipation and shock absorption has:
- a first layer 40 formed of a thermal and electrically insulating paste deposited on the upper face of the electronic board. If electronic components are mounted on this face, the paste coats them when it is deposited;
- a second, metal layer 41 of high thermal conductivity deposited on the upper face of the first layer;
- a third layer 42, which is likewise formed of a thermal paste and is deposited on the upper face of the second layer, its upper face coming into contact with the internal wall of the upper part of the housing.

The first layer 40 and the third layer 42 can be made from one and the same thermal paste. For the third layer 42, this material is chosen to ensure excellent thermal conductivity and to have a sufficiently deformable composition for absorbing shocks.

In a non-limiting manner, the material chosen to produce the thermal paste may be filled silicone. It may thus contain zinc oxide, in addition to the silicone that is used as binding agent allowing the thermal conductivity to pass from 0.2 W/m/K to values of between 3 and 5 W/m/K. If the electrical insulation of the components is provided by a varnish of the acrylic type or an epoxy layer, other thermal pastes can also be cited with thermal conductivities ranging up to 12 W/m/K. The material "Prolimatech PK1" (registered trade mark) is composed of 60 to 85% aluminium, 15-25% zinc oxide, 12-20% silicone oil and finally an antioxidant. Some thermally conductive pastes, such as "Arctic Silver 5" (registered trade mark) additionally contain particles of silver. Others make use of graphite, such as the paste referenced "WLPG 10" (registered trade mark) from Fischer Elektronik, the latter not using silicone and exhibiting excellent thermal conductivity (10.5 W/m/K). Finally, it is also known to add carbon nanoparticles.

According to one particular feature, the thermal paste employed has a thermal conductivity of between 1 and 12 W/m/k.

The second layer 41 employed is advantageously a metal layer in order to incorporate a material of high thermal conductivity into the module 4 for heat dissipation and shock absorption. It may be a plate of copper, gold or aluminium. The second layer may have a thickness of between 0.1 and 0.6 mm. Since this second layer proves to be relatively rigid, the third layer, which is made of a more flexible and deformable material, is necessary to ensure a shock-absorbing function and to provide an implantable device that has a level of deformability greater than a device having only one metal layer disposed between the board and the cover.

Figure 1B:
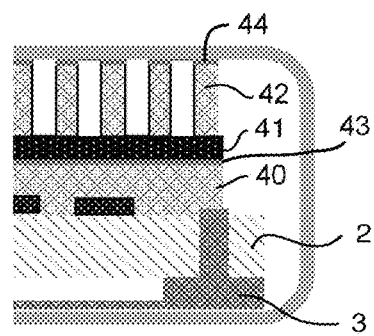
FIG. 1B shows, schematically, in cross section, an optional architecture of the implantable meidcal device according to the invention.

Optionally, in order to improve heat transfer, the module 4 for heat dissipation and shock absorption may have one or more additional layers made of pyrolytic graphite, deposited under the layer of copper and optionally between the third layer 42 and the internal wall 10 of the cover of the housing. Pyrolytic graphite layers 43 and 44 are shown in FIG. 1B.

According to one particular aspect of the invention, the third layer 42, which is made of thermal paste, is said to be structured. The term "structured" means that it has a plurality of cavities in order to improve its deformability and thus to better protect the electronic assembly from shocks. The structure is thus produced so as to alternate full parts and recessed parts.

The cavities may or may not be through-cavities (that is to say made all the way through the thickness of the layer). The structure of the third layer 42 may have a mixture of several cavities, some of them being through-cavities and others not being through-cavities.

FIGS. 2A to 2D show several examples of possible structures in the third layer.

Figure 2A:
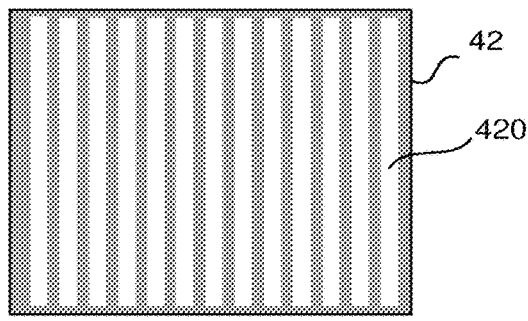
FIGS. 2A to 2D show three examples of possible structuring of the third layer employed in the device of the invention.

In FIG. 2A, the structure is said to be comb-like. Thus, it has a plurality of parallel rectilinear through-trenches 420, thereby forming a plurality of parallel crosspieces or teeth.

Figure 2B:
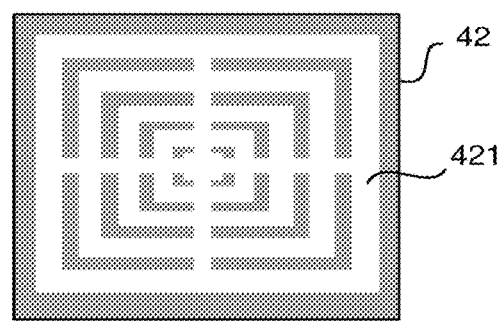

In FIG. 2B, the structure has a plurality of rectangular through-cavities 421 disposed concentrically. Two cavities following two mutually perpendicular rectilinear trenches may also be added.

Figure 2C:
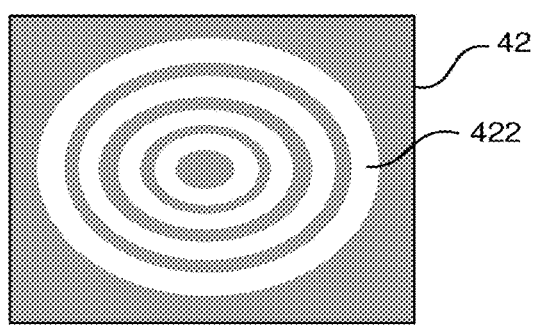

In FIG. 2C, the structure has a plurality of circular or elliptical through-cavities 422 disposed concentrically.

Figure 2D:
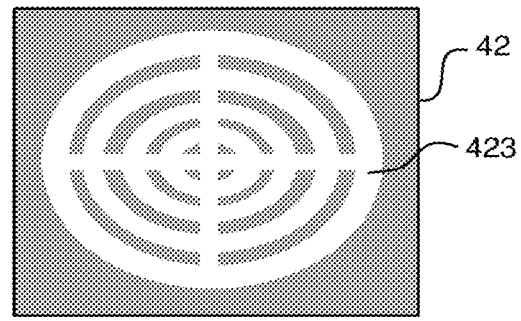

In FIG. 2D, the structure has a plurality of circular through-cavities 423 disposed concentrically, two rectilinear and mutually perpendicular trenches being added.

Figure 5:
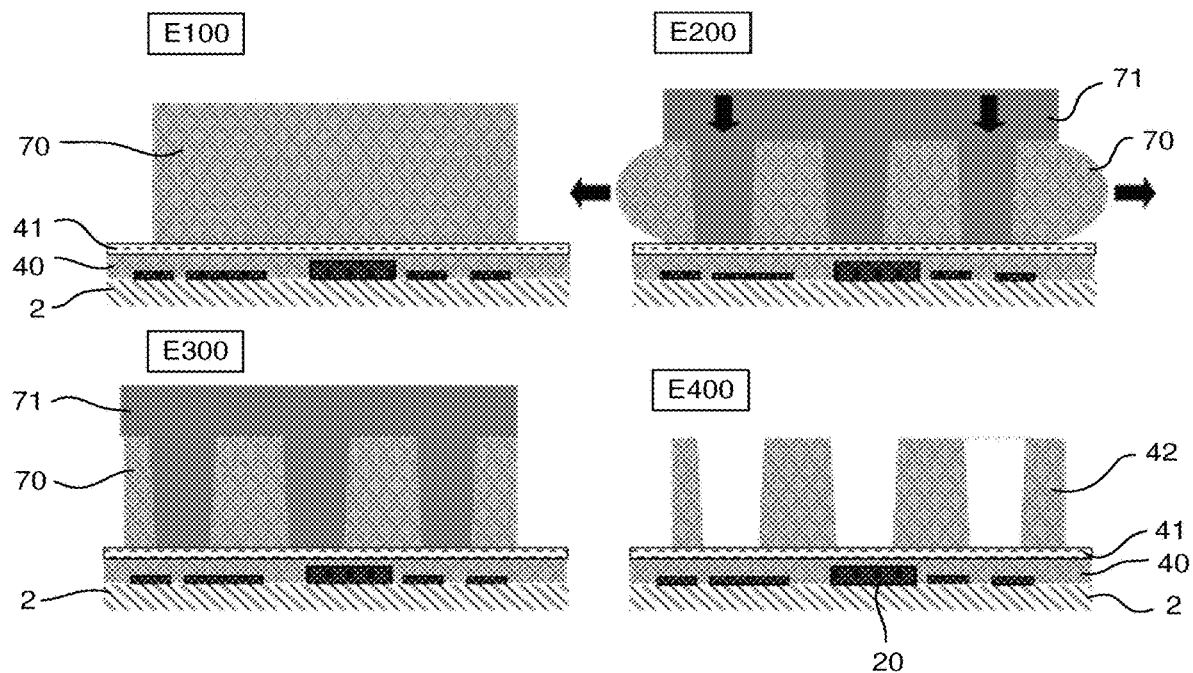

Several methods may be envisaged to produce the structure in the third layer. FIGS. 3 to 5 show several different methods for producing a comb-like structure, such as the one shown in FIG. 2A, in a thermal paste.

FIG. 3 shows a first production method. This first method comprises the following steps:

E1: A layer 50 of thermally conductive paste to be structured is deposited uniformly on a substrate 51. The thickness of the layer 50 may be rendered uniform by means of a doctor blade or a plate abutting a shim.

E2: The structure is produced by employing a tool 52 provided advantageously with a plurality of punches. The punches advantageously have a shape adapted to the final structure to be produced, for example in the form of a comb, ring, rectangle, etc. The tool is applied through the layer of material such that the punches pass through said layer.

E3: The withdrawal of the tool 52 makes it possible to remove the material and to obtain the desired structure.

E4: The structured layer 50 obtained can then be attached to the second layer 41 of the module for heat dissipation and shock absorption, in order to become the third layer 42 thereof.

FIG. 4 shows a second method for producing the structured layer. This solution can be used directly on the second layer 41 of the module 4 for heat dissipation and shock absorption or on a separate substrate.

E10: A negative structure that is chemically soluble or preferably liquefiable at temperature is used. This negative structure may be a heat-sensitive mould 60 made of wax or paraffin (solid/liquid transition temperature close to 45° C.), which comprises a base and structures in relief.

E20: Once the mould 60 has been applied to the second layer 41, a given quantity of thermal paste 61 is injected.

E30 and E40: The assembly is heated until the mould 60 employed has partially or completely dissolved. All that then remains is the desired structured layer 42, once the mould has disappeared.

FIG. 5 shows a final method for generating the structure in the third layer of the module.

E100: A layer 70 of thermal paste is deposited directly, with a uniform thickness, on the second layer 41 of the module 4.

E200: A mould 70 is applied to the layer 70 by compression until it passes through the latter. The mould 70 has a shape adapted to the structure to be obtained.

E300: The excess material released by the compression is removed.

E400: The mould 70 is withdrawn so as to obtain the third layer 42 with the chosen structure.

Figure 6A:
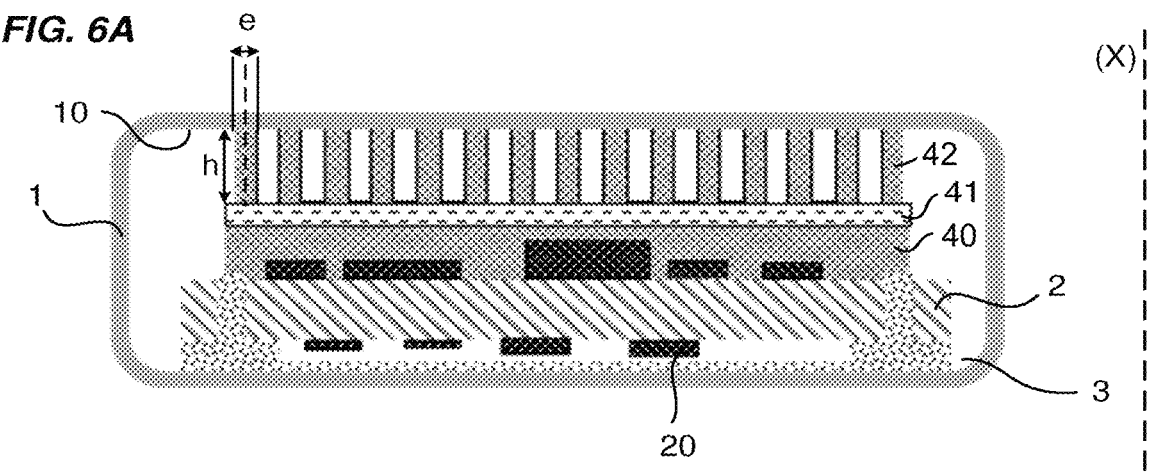
FIGS. 6A to 6C and 7A to 7C illustrate the principle of shock absorption permitted by virtue of the device of the invention.
Figure 6B:
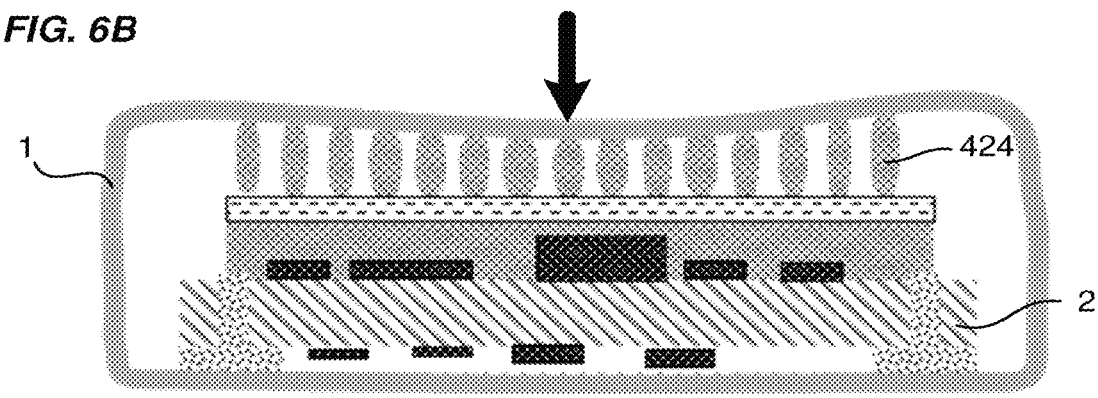
Figure 6C:
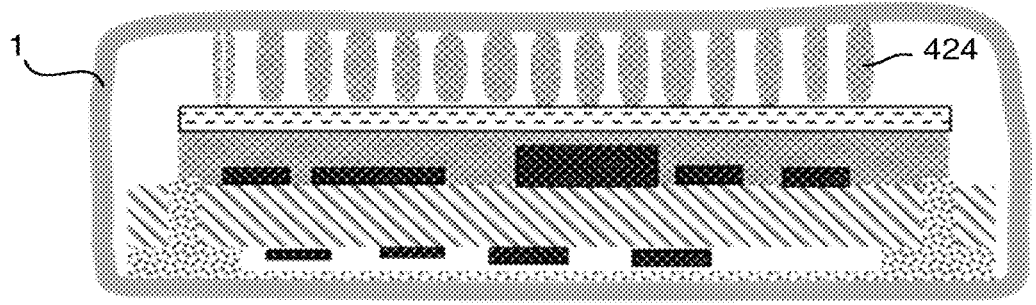

FIGS. 6A to 6C show the device according to the invention subjected to a deformation that goes beyond its elastic limit, showing the principle of mechanical absorption permitted by the device. In these figures, the structure has a form as in FIG. 2A, which is comb-like with several parallel crosspieces.

When the housing 1 is subjected to a mechanical load, it firstly deforms in the elastic domain (reversible deformation) and then in the plastic domain (irreversible deformation). The challenge of the invention is thus to absorb some of the deformation energy in order to avoid damaging the electronics in the housing and compromising the hermeticity of the device.

In FIG. 6A, a mechanical shock is applied to the upper face of the cover of the housing 1 (along the vertical arrow).

In FIG. 6B, the mechanical shock brings about deformation of the housing 1 and thus compression of the crosspieces 424 of the structure of the third layer 42.

In FIG. 6C, after the mechanical shock, the housing 1 returns to its initial form if there has been no plastic deformation. The module 4 for heat dissipation and shock absorption, notably the structured third layer 42 thereof, will have been able to absorb some of the energy and to limit the deformation of the housing and to avoid the latter damaging the electronic part of the device.

Figure 7A:
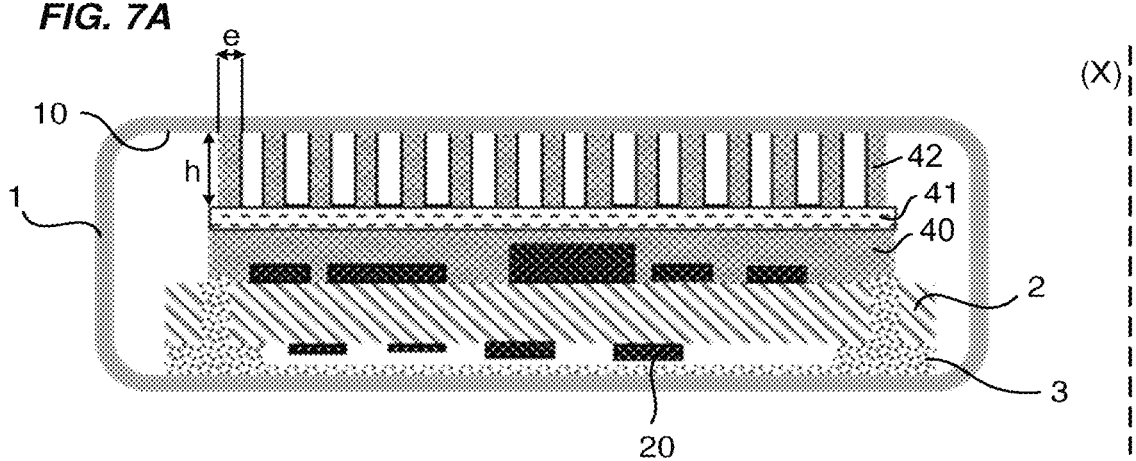
Figure 7B:
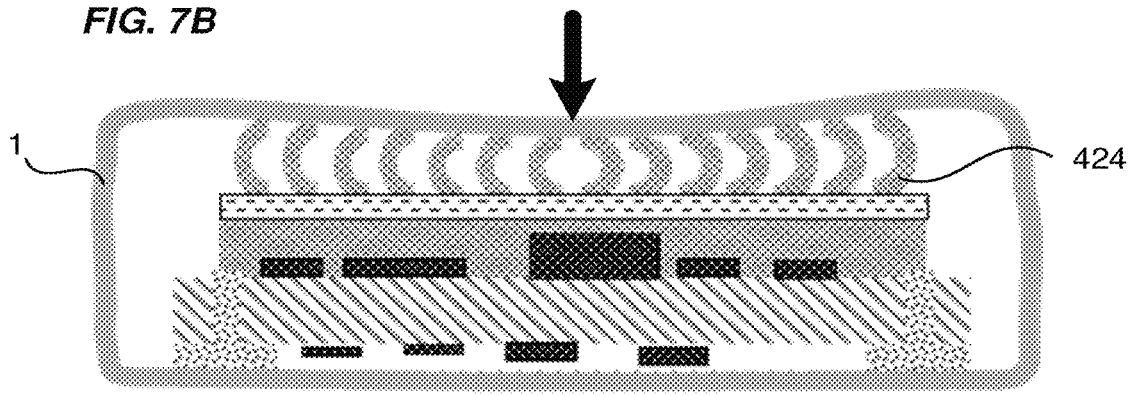
Figure 7C:
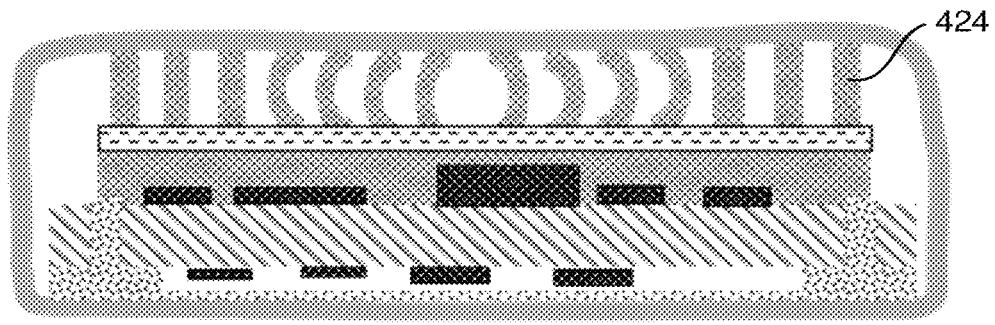

In FIGS. 7A to 7C, the principle is the same as above, except that the structure of the third layer 42 does not deform in compression but by buckling. In FIG. 7B, it is thus possible to see the buckling undergone by the crosspieces 424 of the structure 42.

Each tooth of the comb of the structure of the third layer, having a height h and a width e, is subjected to a dynamic compressive load. In a steady state, the deformation of the tooth is uniform and symmetric with respect to the neutral axis. If the elongation (h/e) is very high (>10), buckling may occur at the tooth, and the latter thus deforms mainly on one side. During the post-collapse phase, a great deal of energy is dissipated by plastic deformation.

This critical load for buckling F depends on the Young's modulus of the material, on the conditions of fastening of the ends that define the buckling length ($l_k$=h for a beam ball-jointed at its two ends) and on the axial moment of inertia I of the beam (and thus on the coefficient e and the depth p of the comb), according to the relationship:

$$F = \frac{\pi^2 EI}{l^2}$$

If this relationship is applied to a single tooth, for a Young's modulus of 1 MPa, a height of 3 mm, a comb width of 0.3 mm and a depth of 10 mm, it is found that $F_{critical}$=0.025 N.

This force is greater than a factor n, where n is the number of teeth, which is also dependent on the resolution of the production method.

In order to quantify the energy absorption of the structured thermal paste and the influence of the shape factors h, p and e, simulations were carried out.

A first type of simulation was established to compare the behaviour of the non-structured thermal paste with that of the structured thermal paste.

The non-structured thermal paste was considered to be a hexahedron with the dimensions: depth 10×width 4.8×height 3 mm³.

For a comb-like structured thermal paste, the teeth have a thickness e=h/10=0.3 mm (h=3 mm and p=10 mm). This comb is made up of 8 identical teeth.

These two structures were subjected to an impact energy of 75 mJ (block of mass 6 g impacting the thermal paste at a speed of 5 m/s).

The results show that the structured thermal paste absorbs 50% of the impact energy, whereas the non-structured thermal paste only absorbs 27% thereof.

The results thus indicate that structuring of the thermal paste in the third layer 42 can indeed give it improved energy absorption properties.

It will be understood from the above that the device according to the invention has numerous advantages, including the following:

It is capable of ensuring good heat dissipation;
It ensures protection of the internal electronics from acute shocks and even from irreversible plastic deformations;
It is easy to produce and uses conventional materials.

The invention claimed is:
1. An implantable medical device comprising:
a hermetic housing defining an internal space, at least one electronic board housed in said internal space of the housing, said board supporting electronic components, a module for heat dissipation and shock absorption, housed in the internal space of the housing and arranged between said electronic board and an internal wall of the housing, and wherein said module for heat dissipation and shock absorption comprises:

a first layer of thermal paste placed in the internal space of the housing and deposited on said electronic board, a second, metal layer of high thermal conductivity deposited on said first layer, a third layer of thermal paste deposited on said second layer and positioned so as to come into contact with said internal wall of the housing, said third layer having a structure with a plurality of cavities distributed over the entire area of contact of the third layer with the internal wall of the housing.

2. The device according to claim 1, wherein the structure of the third layer is realized in the form of a plurality of concentric cavities.

3. The device according to claim 1, wherein the structure of the third layer has a plurality of parallel rectilinear cavities that form trenches and a comb structure having a plurality of teeth of given height and width.

4. The device according to claim 1, wherein the structure of the third layer has a spiral.

5. The device according to claim 1, wherein each cavity of the structure is a through-cavity.

6. The device according to claim 1, wherein the second layer is formed of copper, gold or aluminium.

7. The device according to claim 1, wherein the thermal paste of the first layer and of the third layer has a thermal conductivity of between 1 and 12 W/m/K.

8. The device according to claim 1, wherein the first layer and the third layer include filled silicone.

9. The device according to claim 1, wherein the module for heat dissipation and shock absorption includes one or more additional layers made of pyrolytic graphite that are deposited under the second layer and between the third layer and the internal wall of the housing.

10. A method for manufacturing an implantable medical device as defined in claim 1, wherein the structure of the third layer is produced by applying punches to a layer of thermal paste deposited on a substrate, by compression moulding or by injection moulding in a chemically soluble or thermally liquefiable mould.

* * * * *